US008263023B2

(12) United States Patent
Le Vot et al.

(10) Patent No.: US 8,263,023 B2
(45) Date of Patent: Sep. 11, 2012

(54) MICROFLUIDIC SYSTEM AND METHOD FOR SORTING CELL CLUSTERS AND FOR THE CONTINUOUS ENCAPSULATION THEREOF FOLLOWING SORTING THEREOF

(75) Inventors: Sophie Le Vot, Le Pont de Claix (FR); Jean Berthier, Meylan (FR); Florence Rivera, Meylan (FR)

(73) Assignee: Commissariat a l'Energie Atomique, Paris (FR)

( * ) Notice: Subject to any disclaimer, the term of this patent is extended or adjusted under 35 U.S.C. 154(b) by 382 days.

(21) Appl. No.: 12/437,901

(22) Filed: May 8, 2009

(65) Prior Publication Data

US 2009/0286300 A1 Nov. 19, 2009

(30) Foreign Application Priority Data

May 13, 2008 (FR) .................................... 08 02575

(51) Int. Cl.
*G01N 15/06* (2006.01)
*G01N 33/00* (2006.01)
*G01N 33/48* (2006.01)

(52) U.S. Cl. ........ 422/503; 422/502; 422/504; 422/509; 436/43; 436/52; 436/53; 436/174; 436/176

(58) Field of Classification Search .................. 422/502, 422/503, 504, 509; 436/43, 52, 53, 174, 436/176
See application file for complete search history.

(56) References Cited

U.S. PATENT DOCUMENTS

| | | | | |
|---|---|---|---|---|
| 6,007,690 | A * | 12/1999 | Nelson et al. | 204/601 |
| 6,132,685 | A * | 10/2000 | Kercso et al. | 422/566 |
| 6,540,895 | B1 * | 4/2003 | Spence et al. | 204/450 |
| 2004/0126279 | A1 * | 7/2004 | Renzi et al. | 422/100 |
| 2006/0051329 | A1 * | 3/2006 | Lee et al. | 424/93.7 |
| 2006/0290745 | A1 * | 12/2006 | Feng et al. | 347/65 |
| 2007/0009668 | A1 | 1/2007 | Wyman et al. | |
| 2007/0125941 | A1 | 6/2007 | Lee et al. | |

(Continued)

FOREIGN PATENT DOCUMENTS

EP 1 533 605 5/2005

(Continued)

OTHER PUBLICATIONS

International Search Report for French Application No. 08/02575, filed May 13, 2008.

(Continued)

*Primary Examiner* — Brian J Sines
(74) *Attorney, Agent, or Firm* — Alston & Bird LLP

(57) ABSTRACT

A microfluidic system and method for sorting cell clusters, and for the continuous and automated encapsulation of the clusters, once sorted, in capsules of sizes suitable for those of these sorted clusters is provided. The microfluidic system comprises a substrate in which a microchannel array comprising a cell sorting unit is etched and around which a protective cover is bonded, and the sorting unit comprises deflection means capable of separating, during the flow thereof, relatively noncohesive cell clusters, each of size ranging from 20 μm to 500 μm and of 20 to 10 000 cells approximately, such as islets of Langerhans, at least two sorting microchannels arranged in parallel at the outlet of said unit being respectively designed so as to transport as many categories of sorted clusters continuously to a unit for encapsulation of the latter, also formed in said array.

11 Claims, 10 Drawing Sheets

U.S. PATENT DOCUMENTS

2009/0181864 A1* 7/2009 Nguyen et al. .................. 506/33

FOREIGN PATENT DOCUMENTS

WO WO 02/44689 6/2002

OTHER PUBLICATIONS

De Vos, Paul, et al., Article, Association Between Capsule Diameter, Adequacy of Encapsulation, and Survival of Microencapsulated Rat Islet Allografts [Experimental Transplantation], *Transplantation—The Official Journal of the Transplantation Society*, Oct. 15, 1996, pp. 893-899, Transplantation, vol. 62(7), Wolters Kluwer Health, Lippincott Williams & Wilkins, Groningen, The Netherlands.

Lehmann, Roger, et al., Article, Superiority of Small Islets in Human Islet Transplantation, *Diabetes*, Mar. 2007, pp. 594-603, vol. 56, The American Diabetes Association (2007).

Zimmermann, H., et al., Article, Fabrication of Homogeneously Cross-Linked, Functional Alginate Microcapsules Validated by NMR-, CLSM- And AFM-Imaging, *Biomaterials 24*, 2003, pp. 2083-2096, Elsevier Science Ltd., 2003.

Goosen, Mattheus, et al., Electrostatic Droplet Generation for Encapsulation of Somatic Tissue: Assessment of High-Voltage Power Supply, *Biotechnol. Prog.*, 1997, pp. 497-502, vol. 13, American Chemical Society and American Institute of Chemical Engineers, 1997.

Seifert, Douglas, et al., Production of Small, Monodispersed Alginate Beads for Cell Immobilization, *Biotechnol. Prog.*, 1997, pp. 562-568, vol. 13, No. 5, BioProcessing Institute and Chemical Engineering Department, Lehigh University, Bethlehem, PA USA.

Huang, Lotien Richard, et al., Continuous Particle Separation Through Deterministic Lateral Displacement, *Science*, May 14, 2004, pp. 987-990, vol. 304, American Association for the Advancement of Science, Washington, DC USA.

Davis, John, et al., PNAS, Deterministic Hydrodynamics: Taking Blood Apart, *Proceedings of the National Academy of Sciences of the United States of America*, PNAS Oct. 3, 2006, pp. 14779-14784, vol. 103, No. 40, Princeton, NJ.

Inglis, David W., et al., Critical particle size for fractionation by deterministic lateral displacment, paper, Nov. 1, 2005, pp. 655-658, vol. 6, Lab Chip, Princeton, NJ USA.

Yamada, Masumi, et al., Microfluidic Particle Sorter Employing Flow Splitting and Recombining, *Analytical Chemistry.*, Feb. 15, 2006, pp. 1357-1362, vol. 78, No. 4, American Chemical Society, 2006, Tokyo, Japan.

Yamada, Masumi, et al., Pinched Flow Fractionation: Continuous Size Separation of Particles Utilizing A Laminar Flow Profile in a Pinched Microchannel, *Analytical Chemistry*, Sep. 15, 2004, pp. 5465-5471, vol. 76, No. 18, American Chemical Society, Tokyo, Japan.

Yamada, Masumi, et al., Hydrodynamic filtration for on-chip particle concentration and classification utilizing microfluidics, paper, Jul. 1, 2005, pp. 1233-1239, vol. 5, Lab Chip,Tokyo, Japan.

Takagi, Junya, et al., Continuous particle separation in the microchannel having asymmetrically arranged multiple branches, paper, Feb. 2, 2005, pp. 778-784, vol. 5, Lab Chip, Osaka, Japan.

Union Biometrica, Inc., BioSorter™ Instruments, Flow sorting systems for use in Islets of Langerhans research, overview of four experiments, May 2005, pp. 1-10, Union Biometrica, Inc., Holliston, MA USA.

Thorsen, Todd, et al., Dynamic Pattern Formation in a Vesicle-Generating Microfluidic Device, *Physical Review Letters*, Apr. 30, 2001, pp. 4163-4166, vol. 86, No. 18, The Americal Physical Society, Pasadena, CA USA.

Anna, Shelley L., et al., Formation of dispersions using "flow focusing" in microchannels, *Applied Physics Letters*, Jan. 20, 2003, pp. 364-366, vol. 82, No. 3, American Institute of Physics , Cambridge, MA USA.

Sugiura, Shinji, et al., Interfacial Tension Driven Monodispersed Droplet Formation from Microfabricated Channel Array, *Langmuir*, Mar. 6, 2001, pp. 5562-5566, vol. 17, American Chemical Society, Tokyo, Japan.

Sugiura, Shinji, et al., Size control of calcium alginate beads containing living cells using micro-nozzle array, *Biomaterials*, Apr. 9, 2004, pp. 3327-3331, vol. 26, Elsevier Ltd., Tokyo, Japan.

Database WPI Week 200438, *Thomson Scientific*, Jun. 3, 2004, XP-002509076, London, GB.

Fernandez, Luis A., et al., *Transplantation*, Sep. 27, 2005, vol. 80, No. 6, Madison, WI USA.

* cited by examiner

MICROFLUIDIC SYSTEM AND METHOD FOR SORTING CELL CLUSTERS AND FOR THE CONTINUOUS ENCAPSULATION THEREOF FOLLOWING SORTING THEREOF

CROSS REFERENCE TO RELATED APPLICATION

This application claims priority from French Application No. 08 02575, filed May 13, 2008, which is hereby incorporated herein in its entirety by reference.

FIELD AND BACKGROUND OF THE INVENTION

The present invention relates to a microfluidic system and to a method for sorting cell clusters, such as islets of Langerhans, and for the continuous and automated encapsulation of the clusters, once sorted, in capsules of sizes suitable for those of these sorted clusters. The invention applies in particular to the coupling between sorting and encapsulation of such cell clusters, but also, more generally, of cells, of bacteria, of organelles or of liposomes, in particular.

Cell encapsulation is a technique which consists in immobilizing cells or cell clusters in microcapsules, so as to protect them against attacks by the immune system during transplantation. The porosity of the capsules should allow the entry of low-molecular-weight molecules essential to the metabolism of the encapsulated cells, such as molecules of nutrients, of oxygen, etc., while at the same time preventing the entry of substances of higher molecular weight, such as antibodies or the cells of the immune system. This selective permeability of the capsules is thus designed to ensure the absence of direct contact between the encapsulated cells of the donor and the cells of the immune system of the transplant recipient, thereby making it possible to limit the doses of immunosuppressor treatment used during the transplantation (this treatment having strong side effects).

Among the multiple applications of the encapsulation, mention may be made of that of islets of Langerhans, which are clusters of fragile cells located in the pancreas and consisting of several cell types, including β-cells which regulate glycemia in the body by producing insulin. Encapsulation of these islets is an alternative to the conventional cell therapies (e.g. transplantation of pancreas or of islets) used to treat insulin-dependent diabetes, an autoimmune disease in which the immune system destroys its own insulin-producing β-cells.

The capsules produced should meet certain criteria, including biocompatibility, mechanical strength and selective permeability, in particular. Another essential criterion is the size of the capsules, since, by adjusting the size of the cell clusters as well as possible (see reference [1]):

- the amount of “needless” polymer around the cells is reduced, and therefore the response time of the latter is reduced. For example, the regulation of the glycemia by islets of Langerhans encapsulated in capsules of appropriate size will be more rapid, since the glucose will diffuse more rapidly to the islet and the insulin produced will escape therefrom more rapidly;
- the viability of the encapsulated islets is maximized due to the fact that the diffusion of oxygen therein is more rapid, thereby improving the oxygenation of the cells and reducing the risks of appearance of necrosed zones; and
- the volume of capsules to be transplanted is reduced, which can enable the capsules to be implanted in zones more suitable for tissue revascularization. In fact, this revascularization is essential in order to prevent necrosis of the encapsulated cells, since the cells must be located in proximity to the blood network so as to be well supplied with nutrients and with oxygen, in particular. For example, for the treatment of insulin-dependent diabetes, this reduced volume makes it possible to implant the encapsulated islets in the liver or the spleen, regions which are more favorable to revascularization and the peritoneal cavity where capsules are conventionally implanted for reasons of steric hindrance.

While the properties of biocompatibility, mechanical strength or selective permeability appear to be well acquired according to the literature, the same cannot be said of the size of the capsules, which is particularly problematic for the encapsulation of islets of Langerhans. This is because, in all the documents known to the applicant to date, the size of the capsules formed around these islets is fixed and on average of the order of 600 to 800 μm, whereas these islets have a size ranging from 20 to 400 μm only. A capsule size which is fixed and identical whatever the size of the islet therefore poses a problem, all the more so since recent studies have shown that the most effective islets are the smallest ones (see reference [2]).

The principal known encapsulation methods use, according to preference:

- a coaxial liquid or air jet, the capsules produced having a size ranging between 400 μm and 800 μm (however, the average size of the capsules produced is closer to 600-800 μm than to 400 μm);
- a potential difference, which is the encapsulation technique most commonly used when the priority is to reduce the size of the capsules (the size of the capsules ranges, in this case, between 200 and 800 μm); or
- a vibration technique, which has the drawback of sometimes being limited by the viscosities of the solutions used.

The main drawbacks of these techniques are:

- the sizes of the capsules, which are not necessarily suitable for those of the islets of Langerhans to be encapsulated;
- the lack of automation of the encapsulation procedure, where the capsules are gelled while falling into a bath of polycations and are subsequently recovered manually, which generates a heterogeneity in the polymerization time from one capsule to another;
- the size dispersion of the capsules, which increases when the size of the drops decreases; and
- a lack of reproducibility of the capsules produced, which are not necessarily spherical.

Microfluidic systems suitable for size-sorting of bacteria, of cells, of organelles, of viruses, of nucleic acids or even of proteins have recently been developed, and among said systems, mention may be made of:

- those which perform sorting by “deterministic lateral displacement” or “DLD” (see references [6-8] and, for example, document WO-A-2004/037374, US-A-2007/0059781 and US-A-2007/0026381), which are based on the use of a periodic array of obstacles which will disturb or not the path of the particles to be sorted. The particles smaller than the critical size Dc, fixed by the geometry of the device, are not, overall, deflected by these obstacles, such as posts, whereas those larger than this size Dc are deflected in the same direction at each row of posts. The path of the largest particles is therefore in the end deflected relative to that of the smallest, thereby enabling the size-separation of the particles, it being specified that, in the DLD technique, the spacing between two adjacent posts is always greater than the size of the particles to be deflected. This device is suitable for blood samples (separation of red blood cells, white blood cells and of the plasma);

systems which perform sorting by hydrodynamic filtration (see references [9, 10] and documents JP-A-2007 021465, JP-A-2006 263693, and JP-A-2004 154747), which consists in adapting the fluidic resistances of transverse channels by choosing an appropriate rate of flow rates between the main channel and these transverse channels. As a result, the particles of which the size is greater than a critical size (fixed by the value of the fluidic resistance) cannot enter into these transverse channels, even if their size is less than the width of the transverse channels;

simpler systems of sorting by size, using only flow line deflection (see references [11, 12] and, for example, document WO-A-2006/102258) where, in the sorting region, the flow lines are deflected toward a low pressure region: the difference in positioning of the flow lines is accentuated, and since the particles follow the flow lines on which their center of inertia is positioned, the difference in position between small and large particles is accentuated;

sorting systems using filters which make it possible either to allow molecules having a size less than a critical value to pass (see document US-A-2005/0133480), or to allow only the fluid to pass, so as to concentrate the particles or separate the fluid which transports them (see, in this case, document WO-A-2006/079007). The principal limitation of these filter-sorting systems is the risk of clogging of the channels by the particles; and sorting systems where the microfluidic device is coupled to an external field, for instance optical fluorescence or absorbance measurement (see documents WO-A-2002/023163 and WO-A-02/40874), optical traps, dielectrophoresis, conductimetry, potentiometry or amperometry measurements, detection of ligand/receptor binding, etc.

A major drawback of all the microfluidic sorting systems presented in these documents is that they are not at all suitable for sorting cell clusters, such as islets of Langerhans or other relatively noncohesive clusters of similar sizes. In fact, and as explained previously, each of these clusters behaves quite differently from a cell due to its size (from 20 μm to 400 μm for islets of Langerhans, against about ten μm for a single cell) and also due to its weak cohesion (which means that weak shear stresses must be used in the microfluidic sorting system used).

The only system known to the applicant for sorting such cell clusters is the flow cytometry known as "COPAS" which is marketed by the company Union Biometrica. This system, which is not of the microfluidic type, sorts the clusters by size, by measuring their respective times of flight in the beam of a laser radiation (see reference [13]).

Microfluidic encapsulation systems have also recently been developed, which use emulsions that can in particular be formed:

at a T-junction (see reference [14]), at the orifice of a microfluidic flow focusing device, MFFD (see reference [15]), through structured microchannels (cf. reference [16]), or through nozzles (see reference [17]).

These encapsulation systems are the subject of numerous documents, among which are the documents WO-A-2004/071638, US-A-2007/0054119, FR-A-2776535, JP-A-2003 071261 and US-A-2006/0121122 and, more particularly for the encapsulation of cells or cell clusters and the gelling of the capsules formed, the documents US-A-2006/0051329, WO-A-2005/103106 and WO-A-2006/078841.

The gelling step is carried out directly on the microsystem with microchannels in the form of a coil or H-shaped microchannels, as described in documents US-A-2006/0051329 and WO-A-2005/103106.

The principal drawback of these microfluidic encapsulation systems is the same as that mentioned above in the introduction, which is the fact that a single capsule size is obtained whatever the size of the cell clusters. To the applicant's knowledge, only the device of Wyman et al. (see reference [18] and document US-A-2007/0009668) makes it possible to adapt the size of the capsule to the size of the cell clusters, such as islets of Langerhans, by enveloping them in capsules which have a constant thickness in the region of 20 μm, but independently of the size of the islets encapsulated. In the latter document, an aqueous phase is placed above an oil phase and, by adjusting the respective relative densities of these two phases, the islets are found at the water/oil interface. A sampling tube placed in the oil at a certain distance from the interface makes it possible to draw off the aqueous phase and the islets in a fine jet, which, under the effect of the surface tension, breaks up, leaving at the surface of the islets a fine coating of hydrogel of fixed thickness, which is polymerized by UV irradiation. This device is, however, a macroscopic device, and not a microfluidic system.

SUMMARY OF THE INVENTION

One objective of the present invention is to propose a microfluidic system which remedies all the abovementioned drawbacks, which comprises a substrate in which is etched a microchannel array, which comprises a cell-sorting unit and around which a protective cover is bonded.

To this effect, a microfluidic system according to the invention is such that the sorting unit comprises deflection means capable of separating, during the flow thereof, preferably according to the size thereof, relatively noncohesive cell clusters each having a size ranging from 20 μm to 500 μm and from 20 to 10 000 cells, approximately, such as islets of Langerhans, at least two sorting microchannels arranged in parallel at the outlet of said unit being respectively designed so as to transport as many categories of sorted clusters to a unit for encapsulation of the latter, also made in said array.

The term "size" of the cell clusters or of the capsules coating them is intended to mean, in the present description, the diameter, in the case of a substantially spherical cluster or capsule, or more generally the largest transverse dimension of this cluster or of this capsule (e.g. the large axis of an elliptical section in the approximation of an ellipsoid of revolution).

It will be noted that the microchannels dedicated to the sorting of the microsystem according to the invention are capable of separating these cell clusters, such as islets of Langerhans, by deflection, by virtue of their scale, which is quite different from that of the known microfluidic systems which are only suitable for sorting single cells. In fact, the size of these islets ranges in a known manner from 20 to 400 μm, against 1 to 10 μm on average for a cell, and the islets must be handled even more carefully than single cells, because of their fragility and their weak cohesion, which limits the range of shear stresses that can be applied by the sorting unit.

Advantageously, said sorting unit may comprise at least one sorting stage for size-sorting of said clusters, which is designed to generate in said sorting microchannels respectively at least two categories of sizes for said sorted clusters.

It will be noted that the size-sorting stage(s) formed by a given group of microchannels of the system according to the invention make(s) it possible to obtain as many size categories as desired (as a function of the number of sorting microchannels provided for in parallel), and in particular to adapt the size of the capsules formed, subsequent to this sorting, to the size of each category of sorted cell clusters.

It will also be noted that it is possible to couple several successive size-sorting stages (i.e. stages arranged one after the other) so as to optimize the final effectiveness of the sorting unit.

According to one embodiment of the invention, said deflection means of said or of each sorting stage are passive fluidic hydrodynamic means, preferably being of hydrodynamic focusing type, of the type comprising deterministic lateral displacement (DLD) by means of an arrangement of deflection posts that at least one microchannel of this stage comprises, or else of the type comprising hydrodynamic filtration by means of filtration microchannels arranged transversely to a main microchannel.

As a variant, these deflection means, according to the invention, of the or of each sorting stage may be hydrodynamic means coupled to electrostatic or magnetic forces or to electromagnetic or acoustic waves.

According to another characteristic of the invention, an encapsulation unit, capable of automated encapsulation of said sorted clusters as a function of their category, is also formed in said array in fluidic communication with said sorting microchannels, this encapsulation unit being capable of continuously forming, around each sorted cluster, a biocompatible, mechanically strong, selectively permeable monolayer or multilayer capsule.

This encapsulation unit may comprise a plurality of encapsulation subunits which are respectively arranged in parallel in communication with said sorting microchannels so as to form, for each size category of sorted clusters circulating therein, a capsule of predetermined size designed so as to surround each cluster of this category as closely as possible.

Advantageously, each encapsulation subunit may comprise a device for forming said capsules, chosen from the group constituted of T-junction devices, microfluidic flow focusing devices (MFFDs), microchannel (MC) array devices and micronozzle (MN) array devices.

As a variant, each encapsulation subunit may comprise an exchanger of material between an aqueous phase comprising said sorted clusters within each category and a phase that is immiscible with this aqueous phase, for example an oily phase, this exchanger being designed so as to form the capsules by rupturing of the interface between these two phases due to an increased pressure.

According to another characteristic of the invention, said encapsulation unit may also comprise means for gelling the capsules formed, comprising an exchanger of material constituted of microchannels and dedicated to the transfer of these capsules from an encapsulation phase containing them, for example of oil-alginate type, to an aqueous or nonaqueous gelling phase.

It will be noted that the microsystem according to the invention thus makes it possible to entirely automate the cell cluster encapsulation procedure, in the sense that the operator now has only to fill the various reservoirs corresponding to the materials necessary for the encapsulation and recover, at the outlet, the capsules adapted to the size of the presorted clusters.

The microsystem therefore carries out the sorting, capsule formation and gelling steps continuously and in an automated manner, and it can be adapted both to a simple encapsulation and to a multilayer encapsulation. In the latter case, the encapsulation module is complicated by the integration of steps for rinsing the capsules and for bringing into contact with other solutions of polymers or of polycations.

Preferably, there is also formed in said microchannel array a microfluidic transfer module designed so as to transfer said sorted clusters from a culture medium containing them to an encapsulation phase intended to contain them in said encapsulation unit, this transfer module being in fluidic communication with each of said sorting microchannels and being designed so as to minimize the pressure losses in said sorting unit.

In fact, the islets intended for transplantation are conserved in a culture medium, but for the encapsulation, they must be transferred into a polymer solution (fluid most often non-Newtonian, of high viscosity even at low shear stress). In order to automate the encapsulation procedure as much as possible, said transfer module is integrated into the microsystem, between the sorting unit and the encapsulation unit so as to limit the pressure losses in this sorting unit, given the fact that the fluidic resistance is proportional to the viscosity of the solution displaced.

This transfer module also has the advantage of decreasing the total pressure in the microsystem, and therefore of limiting the risks of leaks when the pressures applied are too high.

According to another important characteristic of the invention, said microfluidic system also advantageously comprises a module for coupling said sorting unit to said encapsulation unit, which is designed so as to maintain laminar fluidic conditions in these two units by causing the encapsulation unit to communicate directly or else selectively with the sorting unit.

It will be noted that no known microsystem has thus coupled the sorting step to the encapsulation step. Now, this coupling is not easy to implement, since the fluidics of the sorting unit can disturb the fluidics of the encapsulation unit. It is therefore necessary to model the overall pressure losses (i.e. fluidic resistances) of the microchannels concerned, so as to maintain laminar fluidic conditions in these two units. This modeling is all the more complicated since the encapsulation most commonly uses non-Newtonian polymers (e.g. alginate), the viscosity of which depends on the shear stress applied to the fluid, thereby complicating the modeling of the overall system.

According to one exemplary embodiment of the invention, this coupling module is constituted of intermediate microchannels which respectively connect said sorting microchannels to said encapsulation unit and which have dimensions and a geometry suitable for maintaining said laminar conditions upstream and downstream.

The drawback of this coupling module according to this exemplary embodiment is that, in addition to the precise dimensional design which is required for these intermediate microchannels, a large number of empty capsules may be formed in each encapsulation subunit, which may require, at the outlet of the latter, a final sorting between empty capsules and capsules containing sorted clusters.

According to another preferred exemplary embodiment of the invention, this coupling module comprises buffer microreservoirs for storing the sorted clusters, opening out into each of which is one of said sorting microchannels and which are each connected selectively to the encapsulation unit via an outlet microchannel which is intended to transport the sorted and concentrated clusters and which is equipped with a fluidic valve, for example of air bubble type or of the type comprising a dissolvable blocking gel (preferably comprising an alginate gel, in the case of the use of alginate for the encapsulation), such that the opening and the closing of the valve lowers and raises, respectively, the concentration of the sorted clusters in each microreservoir as a function of the number of capsules undergoing formation in the encapsulation unit.

It will be noted that this preferred fluidic-valve coupling module makes it possible to minimize the formation of empty capsules through this adjustment of the concentration in each microreservoir.

Advantageously, each buffer microreservoir can also have a plurality of fine transverse outlet microchannels which are designed so as to allow expulsion of the phase containing said clusters with the exception of the latter, when said valve is closed.

In general, it will be noted that the microfluidic systems according to the invention must be sterilizable, because it must be possible for the capsules formed by the encapsulation unit to be transplanted into an individual.

A method according to the invention for sorting relatively noncohesive cell clusters of size ranging from 20 μm to 500 μm and of 20 to 10 000 cells approximately, such as islets of Langerhans, consists in circulating these clusters in a microchannel array of a microfluidic system having a geometry suitable for the size and for the number of these clusters to be separated, and in deflecting them from one another according to one of their parameters, such as their size, in such a way as to direct them to at least two sorting microchannels transporting, in parallel, as many categories of sorted clusters, with a view to the encapsulation thereof in this same system.

Advantageously, use is made of at least one stage for size-sorting said clusters in order to generate in said sorting microchannels respectively at least two size categories for said sorted clusters, each stage using:

passive fluidic hydrodynamic deflection, preferably by hydrodynamic focusing, by deterministic lateral displacement (DLD) or by hydrodynamic filtration, or hydrodynamic deflection coupled to electrostatic or magnetic forces or to electromagnetic or acoustic waves.

According to another characteristic of the invention, it is also possible to encapsulate these sorted clusters, in an automated manner, in parallel, as a function of their category, by continuously forming around each sorted cluster a biocompatible, mechanically strong, selectively permeable monolayer or multilayer capsule.

Advantageously, there is then formed, for each size category of sorted clusters, a capsule of predetermined size which surrounds each cluster of this category as closely as possible, preferably with a capsule size of approximately $D_a$+20 μm to $D_a$+150 μm, preferably $D_a$+50 μm, for a category of sorted clusters according to a critical size less than a value $D_a$.

Preferably, these capsules are formed for each category of sorted clusters by means of a device chosen from the group constituted of T-junction devices, microfluidic flow focusing devices (MFFDs), microchannel (MC) array devices and micronozzle (MN) array devices.

As a variant, these capsules can be formed by exchange of material between an aqueous phase comprising the sorted clusters within each category and a phase that is immiscible with this aqueous phase, for example an oily phase, the rupturing of the interface between the two phases by an increased pressure generating these capsules.

According to another characteristic of the invention, the capsules formed are then gelled by transferring these capsules and the encapsulation phase containing them, for example of oil-alginate type, to an aqueous or nonaqueous gelling phase.

The polymer used for the encapsulation may, for example, be an alginate hydrogel, the polymer most commonly used for encapsulation. However, the encapsulation according to the invention is not limited to this hydrogel, and other encapsulation materials could be chosen, such as, in a nonlimited manner, chitosan, carrageenans, agarose gels or polyethylene glycol (PEGs), on condition that the encapsulation unit is adapted to the type of gelling required by the polymer chosen.

Preferably, before each encapsulation, the sorted clusters are transferred from a culture medium containing them to the encapsulation phase intended to contain them, so as to minimize the pressure losses during the sorting.

Also preferably, the method according to the invention also comprises fluidic coupling between the sorting and the encapsulation, which has the effect of maintaining laminar fluidic conditions in the corresponding microchannels, this coupling causing said sorted clusters to communicate directly or else selectively with the encapsulation phase.

As indicated above, this coupling can be carried out by means of intermediate microchannels which have dimensions and a geometry suitable for maintaining the laminar conditions during the sorting and encapsulation.

As a variant, this coupling is preferably carried out by adjusting the concentration of each category, sorted clusters in a buffer microreservoir for storing these clusters which is in communication with one of said sorting microchannels and selectively connected, via said fluidic valve, to an outlet microchannel transporting the sorted and concentrated clusters, the opening and the closing of this valve lowering and raising, respectively, the concentration of the sorted clusters in the microreservoir as a function of the number of capsules undergoing formation, so as to minimize the formation of empty capsules. This microreservoir is also advantageously provided with a plurality of fine transverse outlet microchannels designed so as to expel only the phase containing these clusters without the latter, when the valve is closed.

Advantageously, said sorted cell clusters in the method of the invention are islets of Langerhans which are encapsulated with a capsule size ranging from 70 μm to 200 μm for the islets sorted according to a size of less than 50 μm, with a capsule size that can reach 650 μm for the largest islets sorted according to a size of 500 μm, for example.

One use, according to the invention, of a microfluidic system as presented above consists in sorting either cells, bacteria, organelles or liposomes, or cell clusters, preferably according to categories of interest via adhesion molecules in the first case, or else according to size categories in the case of cell clusters, and then encapsulating them continuously and in an automated manner for each category sorted.

It will in fact be noted that the invention is not limited to only size-sorting and then encapsulation of cell clusters, but it relates, in general, to any coupling of encapsulation with prior sorting of cells, of bacteria, of organelles or of liposomes within a heterogeneous population of these very different particles, in such a way as to encapsulate only the cells/bacteria/organelles/liposomes of interest.

BRIEF DESCRIPTION OF THE DRAWINGS

Other advantages, characteristics and details of the invention will emerge from the further description which follows with reference to drawings attached in the annex, given only by way of examples and in which.

MORE DETAILED DESCRIPTION

Figure 1:
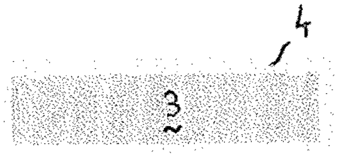
FIG. 1 is a schematic transverse section view of a microfluidic system according to the invention in a first phase of the method for the fabrication thereof, showing the oxidation of the substrate.
Figure 2:
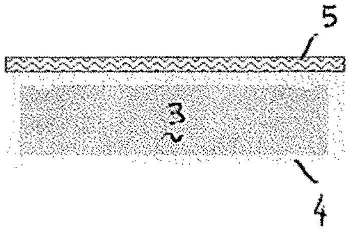
FIG. 2 is a schematic transverse section view of the system of FIG. 1 in a second phase of the method for the fabrication thereof, showing the spreading of a photosensitive resin on this oxidized substrate.
Figure 3:
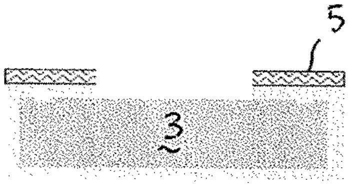
FIG. 3 is a schematic transverse section view of the system of FIG. 2 in a third phase of the method for the fabrication thereof, showing the result of following steps of photolithography and of dry etching, for creating the microchannels.
Figure 4:
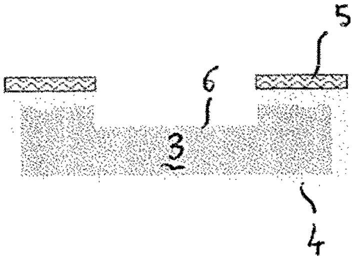
FIG. 4 is a schematic transverse section view of the system of FIG. 3 in a fourth step of the method for the fabrication thereof, showing the result of deep etching steps.

A microfluidic system 1 according to the invention may, for example, be produced, with reference to FIGS. 1 to 7 which give an account of various steps based on known methods of microelectronics on silicon, i.e., in particular, lithography, deep etching, oxidation, stripping and bonding of a protective cover 2 on the substrate 3. This technology on silicon has the advantage of being very accurate (of the order of a micrometer) and non-restrictive both in terms of the etching depths and in terms of the widths of the units. More specifically, the protocol for producing the microsystem 1 is the following:

A deposit of silicon oxide 4 (FIG. 1) is made on the silicon substrate. A photosensitive resin 5 is then deposited by spreading on the front face (FIG. 2), following which the silicon oxide 4 is etched through the layer of resin 5 by photolithography and dry etching of the silicon oxide 4, stopping on the silicon substrate 3 (FIG. 3).

Figure 5:
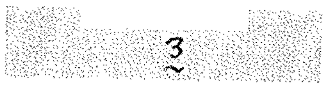
FIG. 5 is a schematic transverse section view of the system of FIG. 4 in a fifth phase of the method for the fabrication thereof, showing the result of a step of stripping the resin and of deoxidation by wet etching.
Figure 6:
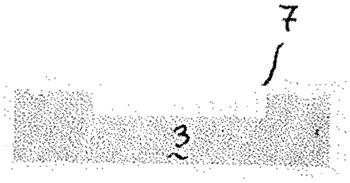
FIG. 6 is a schematic transverse section view of the system of FIG. 5 in a sixth phase of the method for the fabrication thereof, showing the result of an oxidation step.

This substrate 3 is then etched to the desired depth of the microchannels by deep etching 6 (FIG. 4), and the resin is then "stripped" (FIG. 5). The remaining thermal silicon oxide 4 is then removed by deoxidation by means of wet etching (FIG. 5), and then a new layer of thermal oxide 7 is deposited (FIG. 6).

Figure 7:
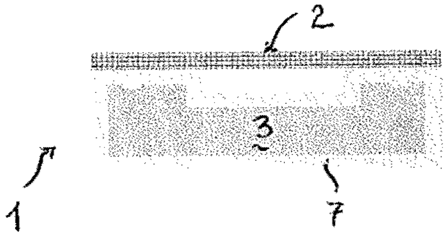
FIG. 7 is a schematic transverse section view of the system of FIG. 6 in a seventh phase of the method for the fabrication thereof, showing the result of a step of bonding a protective cover in order to delimit the section of the microchannels.

The chips obtained are then cut out and a protective cover 2 made of glass—or of another material that is transparent so as to allow observation—is bonded, for example by anodic bonding or direct bonding (FIG. 7).

Before assembly of the microchannels or capillaries (not illustrated), a surface treatment of the hydrophobic silanization type may also be carried out.

The protocol described above is one of the many fabrication protocols that can be followed. Moreover, a material other than silicon, for example a PDMS (polydimethylsiloxane) or else another elastomer, could be used for the substrate 3, by molding on a master (i.e. matrix) prepared beforehand by photolithography, for example. It will be noted that this fabrication technique is very suitable when the microfluidic system comprises a module for coupling between the sorting unit and the encapsulation unit, comprising fluidic valves, with reference to FIGS. 18 and 19.

Figure 8:
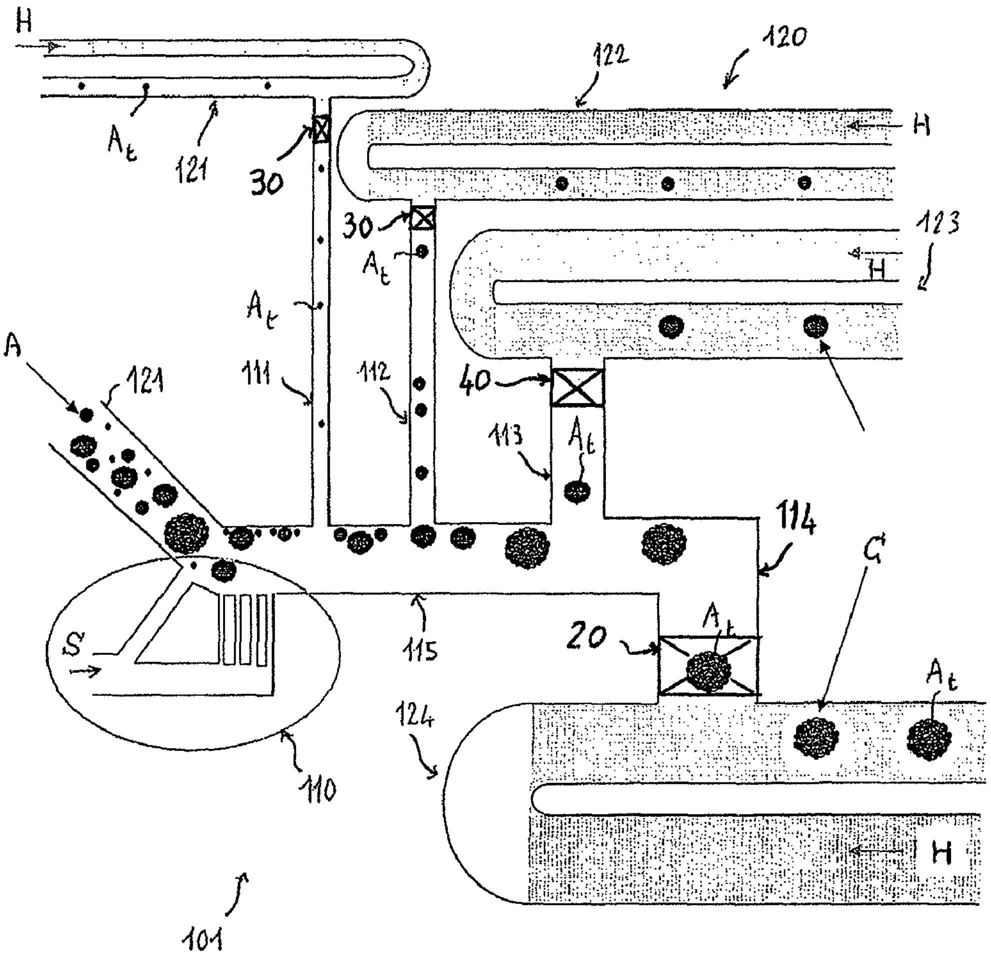
FIG. 8 is a partial schematic view from above of a microfluidic system according to an exemplary embodiment of the invention, showing a unit for sorting by hydrodynamic filtration and a unit for encapsulation via T-junctions, which is coupled thereto.

The microfluidic system 101 according to the example of the invention illustrated in FIG. 8 comprises, on the one hand, a unit 110 for size-sorting clusters A by hydrodynamic filtration, terminating with four transverse sorting microchannels 111 to 114, and an encapsulation unit 120 subdivided into four encapsulation subunits 121 to 124 respectively coupled to these microchannels and transporting as many sorted cluster, At size categories.

Figure 12:
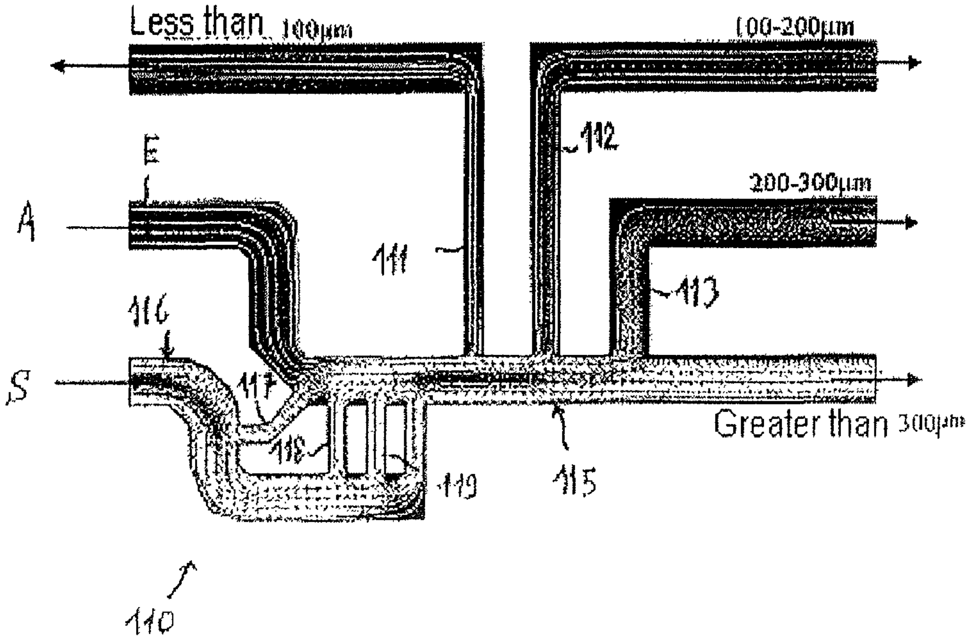
FIG. 12 is an image modeling the flow lines in another example of a sorting unit according to the invention with sorting by hydrodynamic filtration.

The principle of this sorting unit 110 is illustrated in FIG. 12 and is based on focusing of the clusters A at the wall. More specifically in relation to this FIG. 12, the fluidic resistances of the transverse microchannels 111 to 113 are adapted by choosing an appropriate ratio of flow rate between the main microchannel 115 and these transverse microchannels. As a result of this, the clusters A can only enter into one of the transverse microchannels 111 to 113, as a function of their size and of the respective fluidic resistances of these transverse microchannels, which are thus finely calculated in order to determine the size range of clusters A that can enter into any such microchannel 111, 112, 113 or 114.

The solution S for focusing the clusters A at the wall is injected into a secondary microchannel 116 which is in communication with the main microchannel 115 via branches 117 to 119, and this solution S may be the same as that containing the clusters A injected at the inlet E of the unit 110, being for example a culture medium or alginate.

The sorting unit 110 thus makes it possible to sort cell clusters A, such as islets of Langerhans, according to the following four categories:

islets At smaller than 100 μm,
islets At from 100 to 200 μm,
islets At from 200 to 300 μm, and
islets At exceeding 300 μm.

Figure 9:
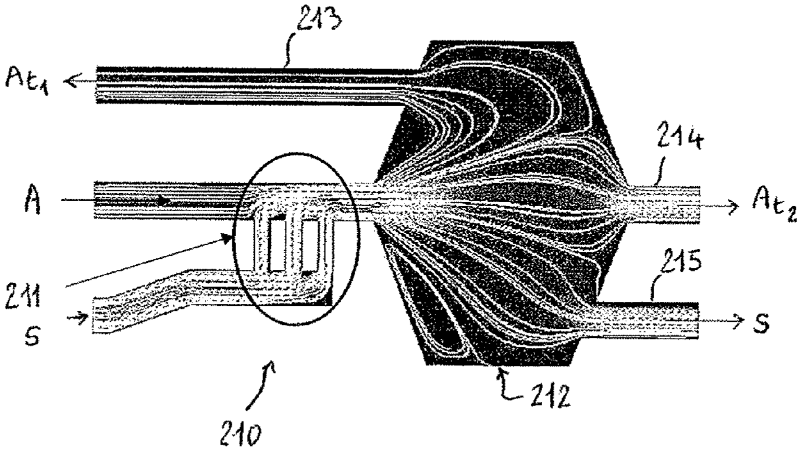
FIG. 9 is an image modeling the flow lines in an example of a sorting unit according to the invention with sorting by hydrodynamic focusing.

As a variant of FIG. 12, it would be possible to use, in a system of FIG. 8, the unit 210 for sorting by hydrodynamic focusing of FIG. 9, in which can be seen the inlet for the unsorted clusters A, a dynamic focusing device 211 using a focusing fluid S and, at the outlet of a deflection zone 212, a first sorting microchannel 213 transporting sorted clusters $At_1$ deflected due to the fact that they are the smallest and a second sorting microchannel 214 transporting the sorted clusters $At_2$ sorted as being the largest, according to the hypothesis that the cell clusters follow the flow lines on which their centers of inertia are positioned. An outlet microchannel 215 for a part of the focusing fluid (devoid of clusters) is also arranged at the outlet of this zone 212.

Figure 10:
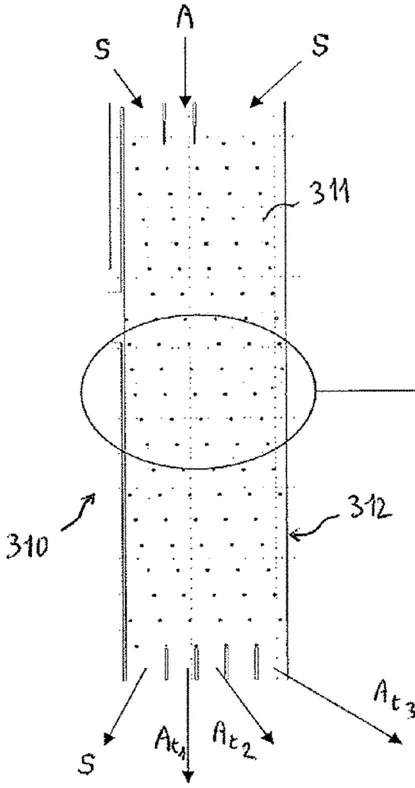
FIG. 10 is a schematic view from above of a microchannel of a sorting unit according to the invention which is equipped with deterministic lateral displacement (DLD) deflection means.
Figure 11:
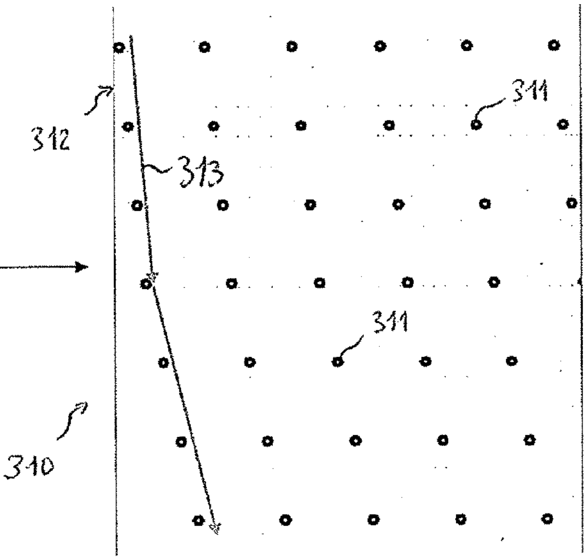
FIG. 11 is a detailed view of the medallion of FIG. 10 showing, symbolically, an example of trajectory deflection obtained by these deflection means.

According to another variant of FIG. 12, it would also be possible to use, in the system of FIG. 8, the unit 310 for sorting by DLD, of FIGS. 10 and 11, using an array of posts 311 which is arranged in a predetermined manner inside a microchannel 312 and the geometric characteristics of which impose a critical size Dc for the cell clusters. The particles smaller than Dc are not deflected by the array of posts 312 and, overall, follow the fluid flow lines, whereas the particles larger than Dc are deflected at each transverse row of posts 312 and, as a result, are separated from the smallest. It will be noted that several sorting stages can be placed in a cascade one after the other. This sorting unit 310 uses a focusing buffer solution F, which is injected at the same time as the solution containing the clusters A to be sorted.

As can be seen in FIG. 10, at the outlet of this unit 310, the buffer solution F without clusters and three categories of sorted clusters $At_1$, $At_2$ and $At_3$, which correspond respectively in this exemplary embodiment to islets of Langerhans smaller than 200 μm, from 200 to 300 μm, and larger than 300 μm, are recovered. Thus, in this example, two sorting stages of different geometric characteristics have been placed in cascade, making it possible to obtain two critical sorting sizes $Dc_1$=200 μm and $Dc_2$=300 μm.

Figure 15:
FIGS. 15 and 16 are respectively two images representing schematically a T-junction and a focusing device of MFFD type, each being intended for the formation of an emulsion in each encapsulation subunit according to the invention.
Figure 16:
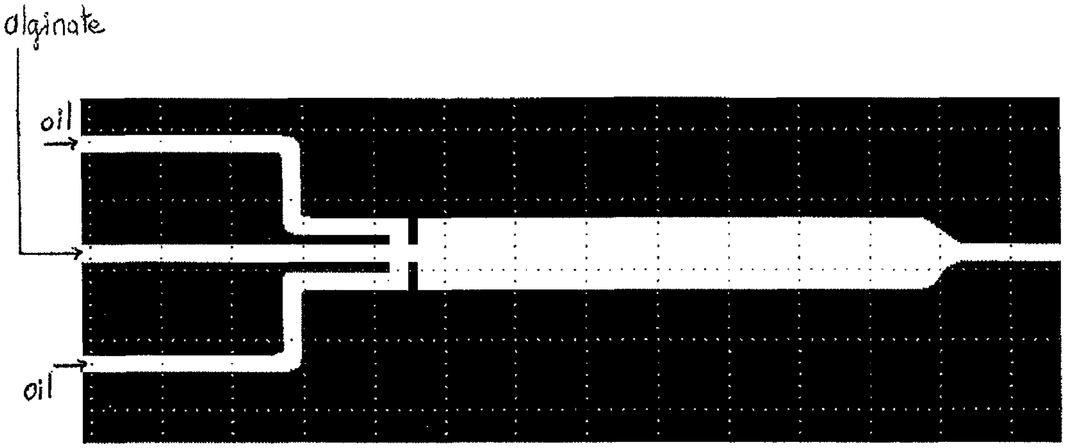

Returning to FIG. 8, the four transverse sorting microchannels 111 to 114 transporting the sorted clusters At open respectively onto the four encapsulation subunits 121 to 124, which are here of T-junction type, through each of which runs an oil H so as to form capsules C, with reference to FIG. 15 which shows, in a known manner, the formation of an emulsion via contact between the two phases of oil and of alginate which come together in this junction. As a variant, it would be possible to replace the T-junctions of FIG. 8 with the MFFD focusing devices of FIG. 16 causing, in this example, two oily phases and one alginate phase to converge.

Figure 17:
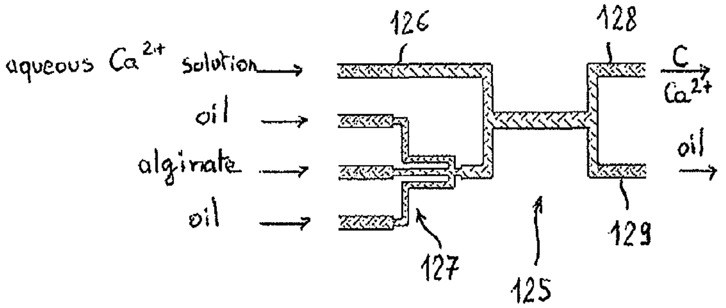
FIG. 17 is a schematic view of a gelling module included in the encapsulation unit according to the invention, for transferring the formed capsules from an oily phase to an aqueous phase.

FIG. 17 shows, by way of example, a possible structure of a gelling module 125 which can be used in each encapsulation subunit 121 to 124 of FIG. 8, and which is capable of transferring alginate-based capsules C from an oily phase to an aqueous phase in order to gel them. This module 125, which is for example on the whole H-shaped, comprises:

connected upstream of an upper end of a vertical foot of the H, an inlet microchannel 126 intended to transport $Ca^{2+}$ ions in aqueous solution and, at the other lower end of this same foot, an encapsulation device 127 of the MFFD type comprising three convergent microchannels, two of which are intended to transport the oily phase and the third of which is intended to transport the alginate, so as to form, in the oil, the Na-alginate-based capsules C, and connected downstream of the upper end of the other vertical foot of the H, an outlet microchannel 128 intended to contain a mixture of the aqueous solution containing the $Ca^{2+}$ ions and these alginate-based, transferred capsules C and, at the lower end of this other foot, a microchannel 129 containing the oily phase.

Figure 17A:
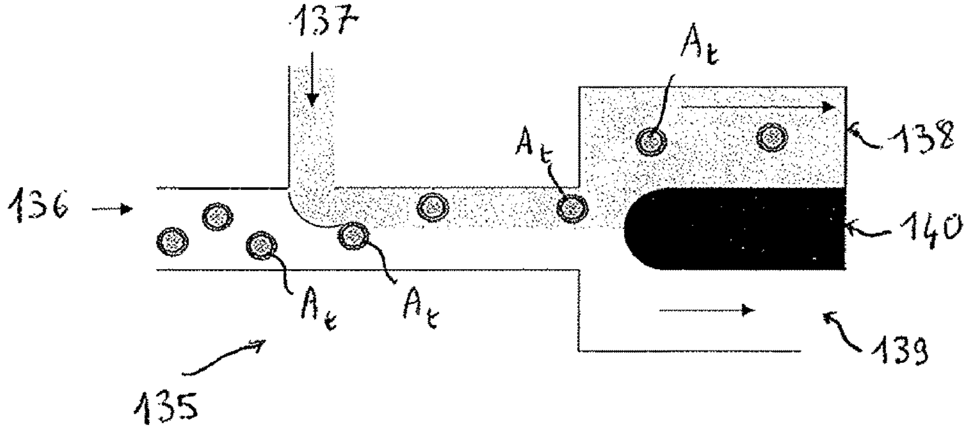
FIG. 17*a* is a schematic vertical section view of a gelling module according to a variant of FIG. 17, which can be included in the encapsulation unit according to the invention.

The gelling model 135 illustrated in the variant of FIG. 17*a* comprises essentially:

two inlets 136 and 137 comprising:
- a horizontal inlet microchannel 136 intended to convey an oily phase containing the cell clusters $A_t$ encapsulated upstream, and
- a vertical inlet microchannel 137 which is in communication with the above microchannel and is intended to transversely inject therein an aqueous phase containing an agent, such as calcium, capable of gelling, by polymerization, the capsules coating these clusters (based on a hydrophilic compound, such as alginate); and two outlets 138 and 139 which are separated from one another by a separator or "wall" 140 (made, for example, of silicon, of glass or of an elastomer such as a PDMS, by way of nonlimiting example) and which comprise on either side of this wall 140:
- an upper outlet 138 intended to transport the aqueous phase containing the encapsulated cell clusters $A_t$, by migration of these clusters from the oily phase to the upper aqueous phase due to the hydrophilic nature of the material (e.g. the alginate) constituting the capsules, and
- a lower outlet 139 for the extraction of the oily phase.

Figure 17B:
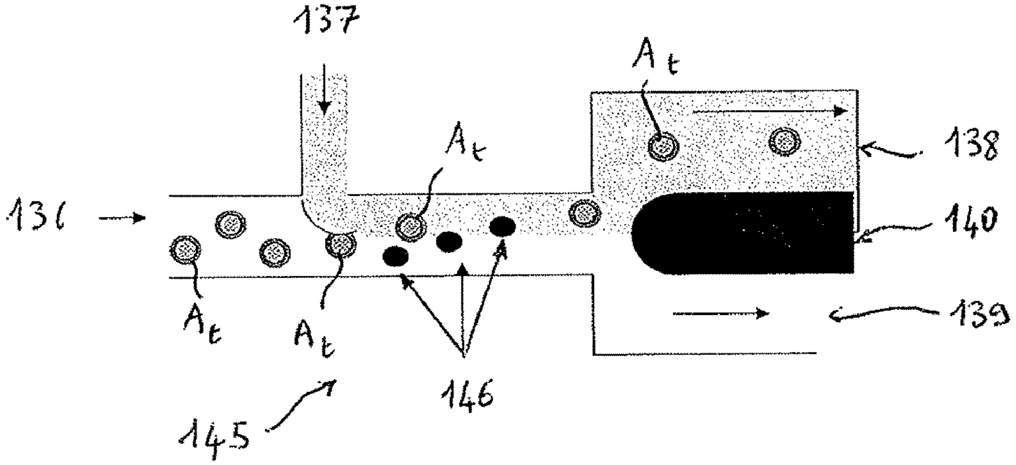
FIG. 17*b* is a schematic vertical section view of a gelling module according to a variant of FIG. 17*a*, which can be included in the encapsulation unit according to the invention.

The gelling module 145 illustrated in FIG. 17*b* differs from that of 17*a* only in that it has, in the zone of the horizontal inlet microchannel 136 which is the site of the abovementioned migration by hydrophilic attraction, an arrangement of trajectory-modifying pillars or posts 146 of the type used in DLD devices (i.e. with a spacing between two adjacent pillars 146 which is greater than the size of the encapsulated clusters $A_t$), making it possible to amplify, through the effect of the deterministic lateral displacement adding to this migration, the lateral displacement of the encapsulated clusters $A_t$ from the oily phase to the upper aqueous phase.

Figure 17C:
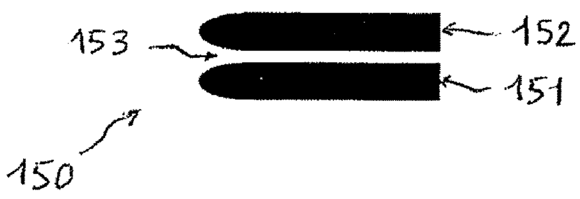
FIG. 17*c* is a partial schematic vertical section view of a variant according to the invention of the separating element planned at the outlet of the gelling module of FIG. 17*a* or 17*b*, FIGS. 18 and 19 are respectively two schematic views of coupling modules according to a first example and a second example of the invention, which are each connected to a sorting stage and to a corresponding encapsulation subunit.

As illustrated in FIG. 17*c*, which shows a variant embodiment of the separator 140 of the gelling module 135, 145 according to FIG. 17*a* or 17*b*, use may advantageously be made of a separator 150 in the form of a "double wall" for optimizing the separation of the aqueous and oily phases. This separator 150 differs from the previous separator only in that it is made up of two superimposed walls or partitions 151 and 152 separated from one another by a central interstitial channel 153, which makes it possible to recover, at the outlet of the module 135 or 145, oily and aqueous phases which are each purer and to eliminate, via this interstitial channel 153, the central aqueous solution/oil interface. More specifically, the planned width of this channel 153 is such that the latter does not transport the encapsulated clusters $A_t$ out of the gelling module 135, 145. It will be noted that this double-partition separator 150 makes it possible in particular to reduce the traces of aqueous solution in the oil, thus allowing re-use of said oil.

Figure 21:
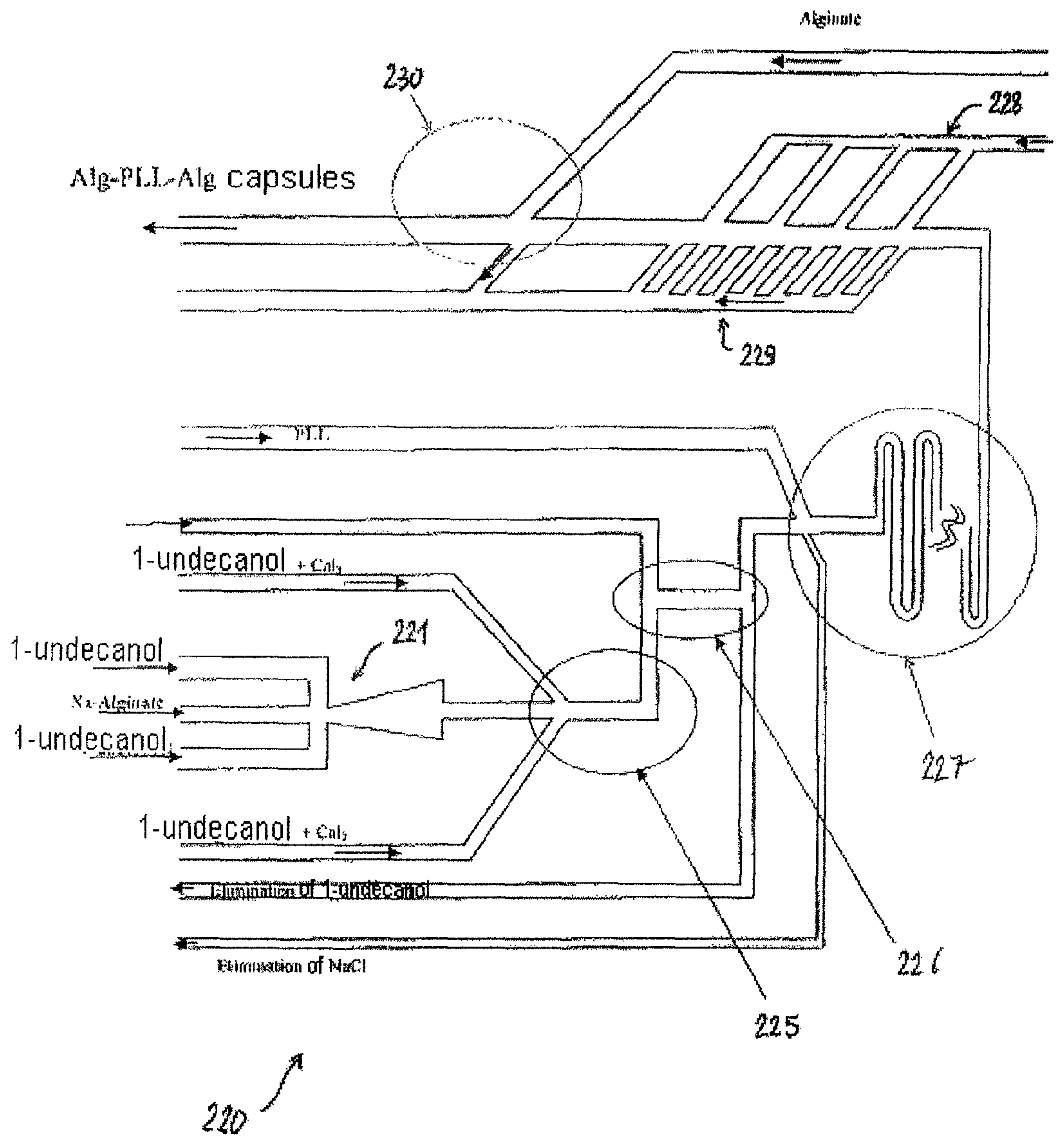
FIG. 21 is a schematic view of an encapsulation unit according to the invention, illustrating in particular the steps of formation of three-layer capsules by means of a focusing device, and the gelling thereof.

As a variant of these FIGS. 17, 17*a*, 17*b* and 17*c*, use may, for example be made, in a nonlimiting manner, of a gelling module 225 included in the unit for encapsulation 220 comprising three alginate-poly-L-lysine-alginate layers according to FIG. 21, where the gelling is carried out directly in 1-undecanol and not in an aqueous phase.

As can be seen in this FIG. 21, the capsules are produced at the level of an encapsulation device 221 of the MFFD type, and then gelled in the module 225 by introducing a stream of 1-undecanol containing $CaI_2$. They are then transferred into an aqueous phase and rinsed, at the level of a first H-shaped rinsing module 226.

The capsules are then brought into contact with a solution of PLL (poly-L-lysine) polycations in a coil-shaped channel 227, which makes it possible to adjust the incubation time for the capsules in this PLL solution. The capsules are subsequently rinsed in a solution of NaCl, in order to eliminate the unbound PLL, in a second rinsing module 228, and the NaCl rinsing solution is then also eliminated in the microchannels 229.

In a final step, the capsules are coated with an external layer of alginate in an attachment module 230, so as to obtain, at the outlet of the unit 220, the three-layer alginate-PLL-alginate capsules.

Figure 13:
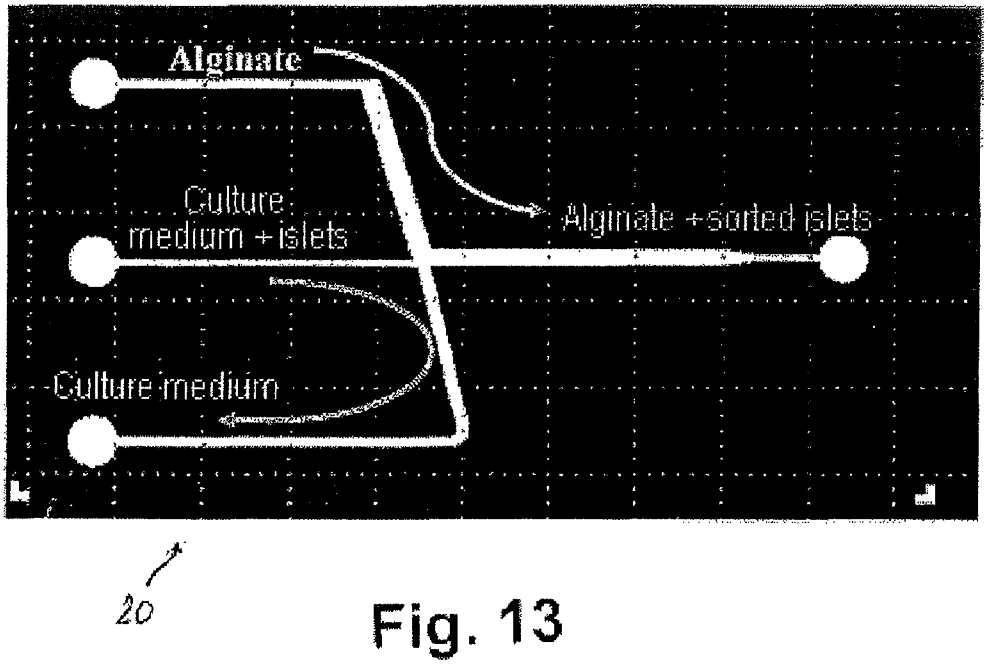
FIG. 13 is an image representing schematically an arrangement of microchannels forming a module for transferring the sorted islets from a culture medium to a solution of alginate used for the encapsulation.

FIG. 13 illustrates a useful structure of a module 20 for transferring sorted cell clusters (e.g. islets of Langerhans) from a culture medium to a solution of alginate used for the encapsulation, which can be advantageously included in a microfluidic system according to the invention. The respective fluidic resistances and sizes of the microchannels forming this transfer module 20 are adjusted such that these sorted clusters are forced to flow in the main microchannel and thus to pass from the culture medium to the solution of alginate (or of another polymer).

Figure 18:
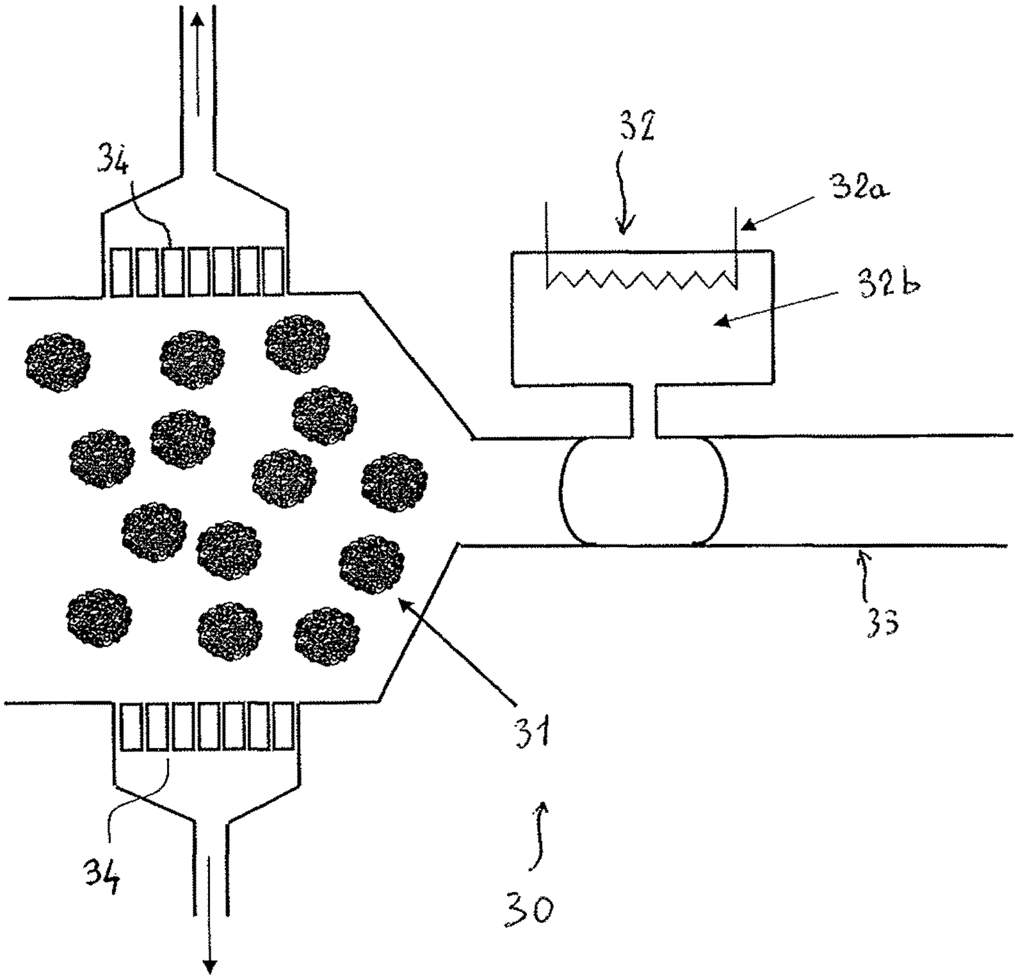
Figure 19:
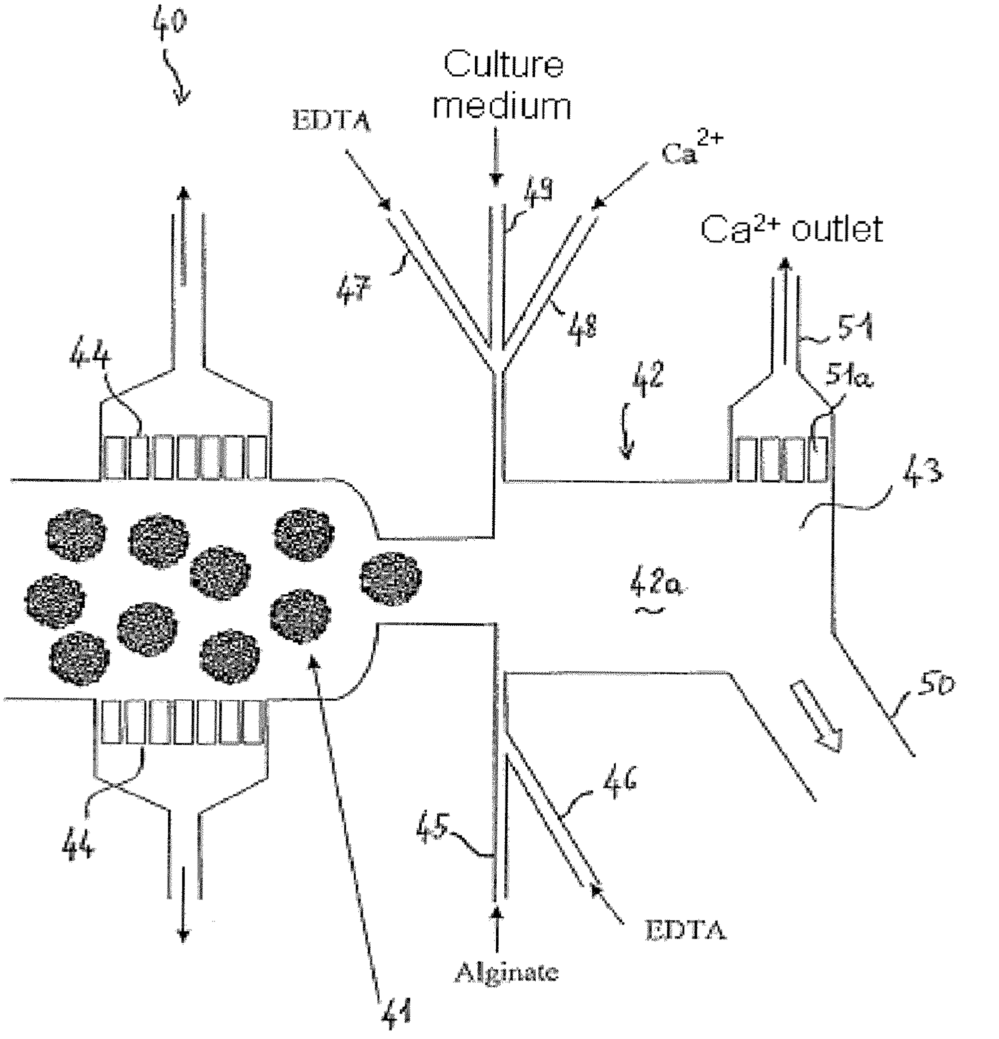

FIGS. 18 and 19 illustrate two preferred examples of coupling modules 30 and 40 which can each be coupled to one of the sorting stages 111 to 114 of FIG. 8 and to each corresponding encapsulation subunit 121 to 124 of this same FIG. 8. Each coupling module 30, 40 is designed so as to maintain laminar fluidic conditions both in the sorting unit 110 and in the encapsulation unit 120, by causing these two units 110 and 120 to selectively communicate with one another.

With reference to these two FIGS. 18 and 19, the corresponding coupling module 30, 40 comprises, in both cases, a buffer microreservoir 31, 41 for storing the sorted clusters, where a sorting microchannel 111 to 114 opens out and which is selectively connected, by means of a fluidic valve 32, 42, to an encapsulation subunit 121 to 124 via an outlet microchannel 33, 50 intended to transport the sorted and concentrated clusters when the valve 32, 42 is open. Each microreservoir 31, 41 also has a plurality of fine transverse outlet microchannels 34, 44 in order to allow the expulsion of the phase containing the clusters without the latter (e.g. the expulsion of the culture medium or of the solution of alginate), when the valve 32, 42 is closed.

The closing of the valve 32, 42 makes it possible to store and especially to concentrate the clusters in such a way that the concentration thereof in the encapsulation solution is sufficient to limit the number of empty capsules formed. The fine microchannels 34, 44 make it possible to see to it that the closing of the valve 32, 42 does not modify the flow lines of the fluid upstream in the corresponding sorting stage (the size of these microchannels 34, 44 is such that the clusters cannot enter therein and are therefore forced to concentrate in the microreservoir 31, 41).

More specifically with reference to FIG. 18, in this example, use is made of a valve 32 of "air bubble" type, the opening and the closing of which are controlled thermally by means of a resistance heating element 32*a* incorporated in a chip, in the following way. When the air is maintained at ambient temperature, the valve 32 is open. If the temperature of the air contained in an activation chamber 32*b* of the valve is increased, this increases the pressure of the gas which is introduced into the outlet microchannel 33 and blocks the passage of the fluid.

More specifically with reference to FIG. 19, in this example, use is made of a valve 42 of the type comprising a dissolvable blocking gel, and preferably comprising an alginate gel. The valve 42 is closed by forming an alginate gel 42*a* by bringing an alginate solution into contact with $Ca^{2+}$ ions. The opening of the valve 42 corresponds to the dissolution of the alginate gel 42*a* by a solution of EDTA or any other $Ca^{2+}$-ion-chelating agent of sodium citrate or EGTA type. By controlling the relative pressures of the EDTA and $Ca^{2+}$ solutions, the amount of each species is controlled in such a way that, if the EDTA is in excess, then all the $Ca^{2+}$ ions are chelated and the alginate gel 42*a* is dissolved by the EDTA, and that, conversely, the free $Ca^{2+}$ ions allow the formation of the gel.

The position of the gel 42*a* is determined by the relative pressures of the alginate, $Ca^{2+}$ and EDTA phases. In order to prevent the microchannel 45 transporting the alginate from blocking, a small amount of EDTA can be introduced at the same time as this alginate.

Once the cluster-concentrating step is complete and the alginate gel 42*a* has been dissolved, the EDTA circulation pressure (EDTA injected into two different microchannels 46 and 47 which are opposite one another relative to the outlet microchannel 43) and the $Ca^{2+}$ ion circulation pressure ($Ca^{2+}$ ions injected into a microchannel 48 adjacent to a microchannel 49 transporting the culture medium) may be virtually zero: only the alginate and this culture medium, which are completely harmless with respect to the viability of the clusters, then circulate in the chamber 43. The latter also has an outlet 50 for conveying the sorted and concentrated clusters to the corresponding encapsulation subunit 121 to 124, and an outlet 51 equipped with fine filtering microchannels 51*a* for expelling only the $Ca^{2+}$ ions.

It will be noted that the main advantage of this type of valve 42 is that there is no technological complication in terms of incorporating into the microsystem according to the invention.

Figure 20:
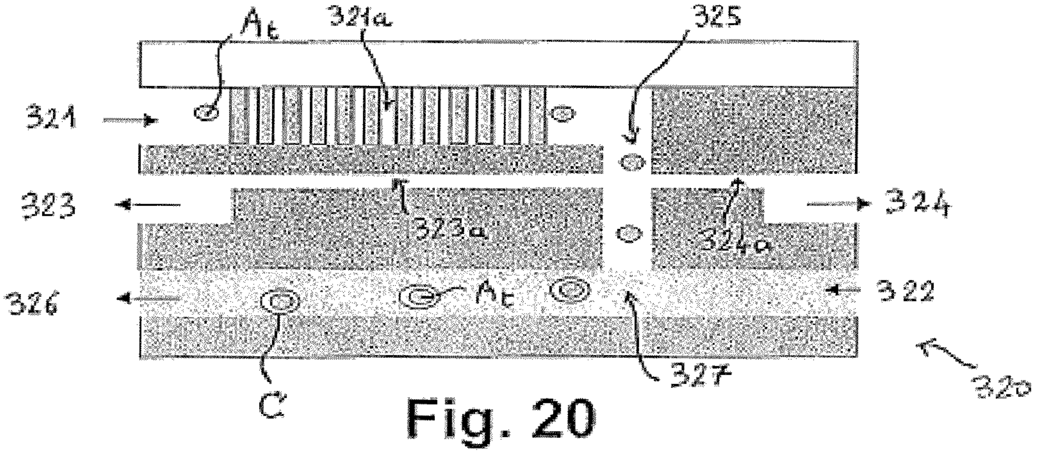
FIG. 20 is a schematic view of a passive fluidic encapsulation unit according to another exemplary embodiment of the invention, subsequent to size-sorting preferably carried out by deterministic lateral displacement (DLD)

FIG. 20 illustrates schematically a variant of an encapsulation unit 320 according to the invention, subsequent to size-sorting performed by deterministic lateral displacement (DLD). The sorted cell clusters At are encapsulated by passive fluidics, the encapsulation being generated on rupturing of the aqueous phase-oil interface when a local increased pressure appears.

More specifically, this encapsulation unit 320 comprises:

a first inlet 321 for an aqueous phase including the sorted clusters At in solution (e.g. in physiological saline, in a culture medium or in alginate, by way of nonlimiting example), this inlet 321 defining a horizontal microchannel 321*a*, a second inlet 322 for a phase which is immiscible with this aqueous phase (e.g. an oil, undecanol, "FC"), this inlet 322 being provided opposite and below the first inlet 321, two opposite outlets 323 and 324 for the aqueous phase introduced via the first inlet 321, which are provided below the latter but above the second inlet 322 and which are connected to one another by two (horizontal) lateral microchannels 323*a* and 324*a* which are in communication with a vertical microchannel 325 extending the microchannel 321*a* at right angles, and an outlet 326 for expelling the immiscible or oily phase containing the encapsulated cell clusters At, which is provided opposite and at the same height as the second inlet 322 for this immiscible phase, forming with said inlet a lower encapsulation microchannel 327 which is in communication with the vertical outlet microchannel 325 that is to receive, by gravity, the clusters originating from the first inlet 321.

It will be noted that this encapsulation unit 320, which is formed in three dimensions (in the sense that the microfluidic inlets and outlets 321, 322, 323, 324 and 326 are not located in the same plane), is capable of forming the capsules C not only through the abovementioned local increased pressure resulting from the obstruction of the two lateral microchannels 323*a* and 324*a*, but also through the force of sedimentation of the cell clusters due to gravity.

Figure 14:
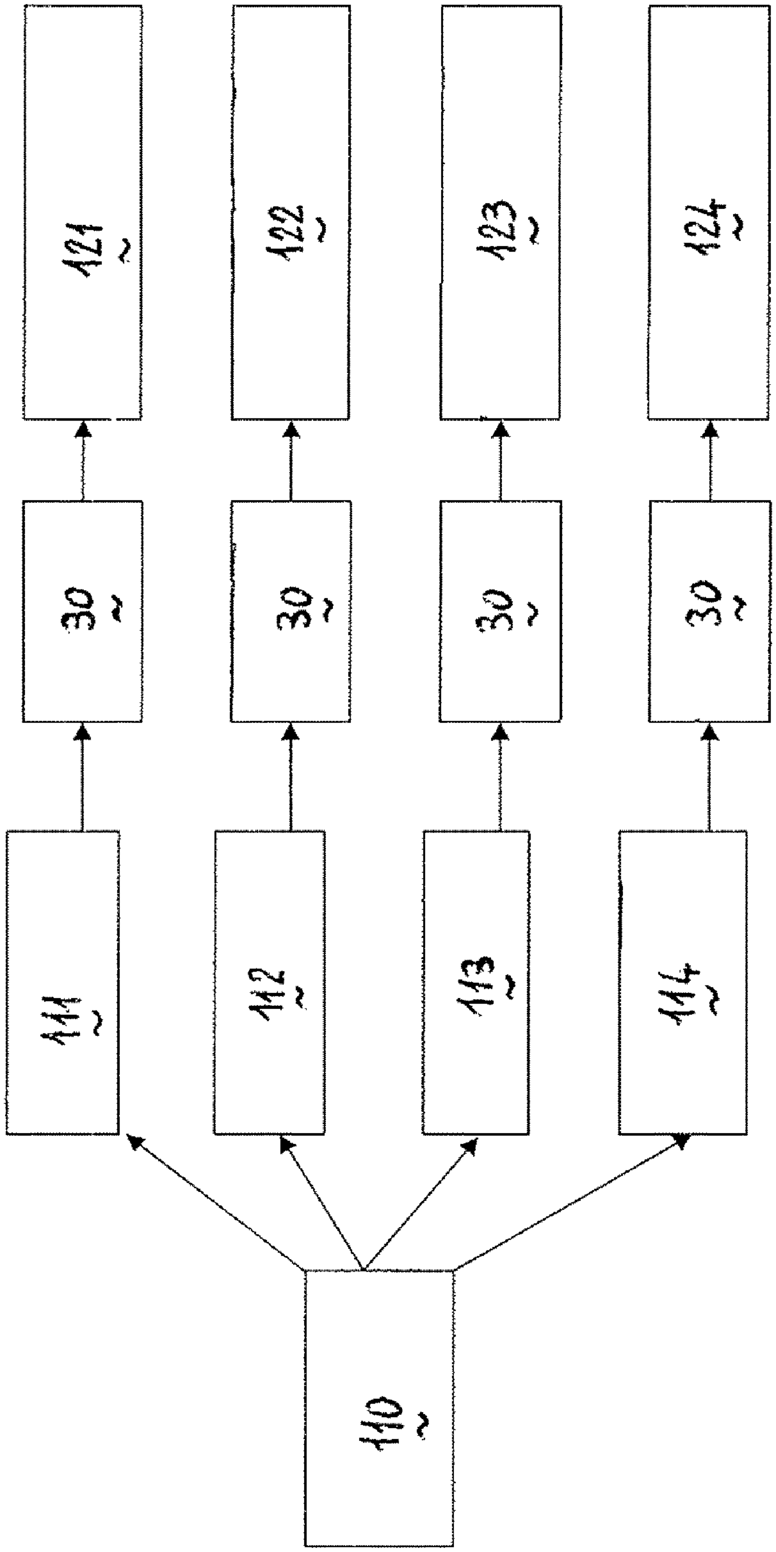
FIG. 14 is a block diagram illustrating four sorting stages respectively coupled to four encapsulation subunits in an example of implementation of the sorting/encapsulation method according to the invention.

In conclusion and as illustrated by way of example in FIG. 14, the sorting/encapsulation method of the invention makes it possible to continuously couple, in an automated manner, a given number of encapsulation subunits 121-124 to as many sorting stages 111-114 of a sorting unit 110, preferably a size-sorting unit, via a corresponding number of coupling modules 30, 40. It is thus possible, for example, to sort islets of Langerhans into four categories respectively associated with matching capsule sizes:

islets of size less than 100 μm sorted in 111 and encapsulated in 121 by capsules 200 μm in diameter;

islets of size between 100 and 200 μm sorted in 112 and encapsulated in 122 by capsules 300 μm in diameter;

islets of size between 200 and 300 μm sorted in 113 and encapsulated in 123 by capsules 400 μm in diameter; and islets of size greater than 300 μm sorted in 114 and encapsulated in 124 by capsules 500 μm in diameter.

In this way, it is understood that the method according to the invention makes it possible to adapt the size of the capsules formed as closely as possible, following sorting of the cell clusters, to the size of the various categories of sorted clusters. This advantageously results in:

minimizing of the amount of polymer to be formed around the clusters and therefore of the response time of the latter, optimizing of the viability of the encapsulated clusters, in particular due to the fact that the diffusion of oxygen therein is more rapid, which reduces the risks of appearance of necrosed areas during transplantations, and minimizing of the volume of capsules to be transplanted, which enables the capsules to be implanted in areas more favorable to tissue revascularization.

LITERATURE REFERENCES CITED

1. De Vos, Association between capsule diameter, adequacy of encapsulation, and survival of microencapsulated rat islet allografts. Transplantation, 1996. 62: p. 893-899.

2. Lehmann, R., Superiority of small islets in human islet transplantation. Diabetes, 2007.56: p. 594-603.

3. Zimmermann, Fabrication of homogeneously cross-linked, functional alginate microcapsules validated by NMR-, CLSM-, and AFM-imaging. Biomaterials, 2003. 24: p. 2083-2096.

4. Goosen, Electrostatic droplet generation for encapsulation of somatic tissue: assessment of high-voltage power supply. Biotechnol. Prog., 1997. 13(497-502).

5. Seifert, Production of small, monodispersed alginate beads for cell immobilization. Biotechnol. Prog., 1997. 13: p. 562-568.

6. Huang, Continuous particles separation through deterministic lateral displacement. Science, 2004. 304(987-990).

7. Davis, Deterministic hydrodynamics: taking blood apart. PNAS, 2006. 103(40): p. 14779-14784.

8. Inglis, Critical particle size for fractionation by deterministic lateral displacement. Lab on a chip, 2006. 6: p. 655-658.

9. Yamada, Microfluidic particle sorter employing flow splitting and recombining. Anal. Chem, 2006. 78: p. 1357-1362.

10. Yamada, Hydrodynamic filtration for on-chip particle concentration and classification utilizing microfluidics. Lab on a chip, 2005. 5: p. 1233-1239.

11. Yamada, Pinched flow fractionation: continuous size separation of particles utilizing a laminar flow profile in a pinched microchannel. Anal. Chem, 2004. 76: p. 5465-5471.

12. Takagi, Continuous particle separation in a microchannel having asymmetrically arranged multiple branches. Lab on a chip, 2005. 5: p. 778-784.

13. Internet site of the company Union Biometrica, the address of which is http://www.unionbio.com/applications/app_notes/app_islet.html 14. Thorsen, Dynamic pattern formation in a vesicle-generating microfluidic device. Physical Review Letters, 2001. 86(18): p. 4163-4166.

15. Anna, Formation of dispersions using "flow focusing" in microchannels. Applied physics letters, 2003. 82(3): p. 364-366.

16. Sugiura, Interfacial tension driven monodispersed droplet formation from microfabricated channel array. Langmuir, 2001. 17: p. 5562-5566.

17. Sugiura, Size control of calcium alginate beads containing living cells using micronozzle array. Biomaterials, 2005.26: p. 3327-3331.

18. Wyman, Immunoisolating pancreatic islets by encapsulation with selective withdrawal. Small, 2007. 3(4): p. 683-690.

The invention claimed is:

1. A microfluidic system comprising a substrate in which an array of microchannels comprising a cell sorting unit is etched and around which a protective cover is bonded, wherein the sorting unit comprises deflection means capable of separating, during the flow thereof, relatively noncohesive cell clusters, each of size ranging from 20 μm to 500 μm and of 20 to 10 000 cells approximately, such as islets of Langerhans, at least two sorting microchannels arranged in parallel at the outlet of said unit being respectively configured to transport as many categories of sorted clusters to a unit for encapsulation of the latter, also formed in said array, said sorting unit comprising at least one stage for size-sorting said clusters which is configured to generate in said sorting microchannels respectively at least two size categories for said sorted clusters, said encapsulation unit comprising a plurality of encapsulation subunits respectively arranged in parallel in communication with said sorting microchannels, each encapsulation subunit being configured to encapsulate a size category of sorted clusters circulating in a corresponding sorting microchannel.

2. A microfluidic system according to claim 1, wherein said deflection means of said or of each sorting stage are passive fluidic hydrodynamic means of the type comprising deterministic lateral displacement by means of an arrangement of deflection posts, wherein at least one microchannel of this stage comprises, or else of the type comprising hydrodynamic filtration by means of filtration microchannels arranged transversely to a main microchannel.

3. A microfluidic system according to claim 1, wherein said deflection means of said or of each sorting stage are hydrodynamic means coupled to electrostatic or magnetic forces or to electromagnetic or acoustic waves.

4. A microfluidic system according to claim 1, wherein each encapsulation subunit comprises a device for forming said capsules, chosen from the group consisting of T-junction devices, microfluidic flow focusing devices, microchannel array devices and micronozzle array devices.

5. A microfluidic system according to claim 1, wherein each encapsulation subunit comprises an exchanger of material between an aqueous phase comprising said sorted clusters within each category and a phase that is immiscible with this aqueous phase, this exchanger being configured to form the capsules by rupturing of the interface between these two phases due to an increased pressure.

6. A microfluidic system according to claim 1, wherein said encapsulation unit also comprises means for a gelling module for gelling the capsules formed in each encapsulation subunit, comprising an exchanger of material constituted of microchannels and dedicated to the transfer of these capsules from an encapsulation phase containing them to an aqueous or nonaqueous gelling phase.

7. A microfluidic system according to claim 1, wherein there is also formed in said microchannel array a microfluidic transfer module configured to transfer said sorted clusters from a culture medium containing them to an encapsulation phase intended to contain them in said encapsulation unit, this transfer module being in fluidic communication with each of said sorting microchannels and being configured to minimize the pressure losses in said sorting unit.

8. A microfluidic system according to claim 1, wherein said coupling modules are configured to maintain said laminar fluidic conditions in these two units by causing the encapsulation unit to communicate directly or else selectively with the sorting unit.

9. A microfluidic system according to claim 8, wherein said coupling module is constituted of intermediate microchannels which respectively connect said sorting microchannels to said encapsulation unit and which have dimensions and a geometry suitable for maintaining said laminar conditions upstream and downstream.

10. A microfluidic system according to claim 8, wherein said coupling module comprises buffer microreservoirs for storing said sorted clusters, opening out into each of which is one of said sorting microchannels and which are each connected selectively to said encapsulation unit via an outlet microchannel which is intended to transport said sorted and concentrated clusters and which is equipped with a fluidic valve, such that the opening and the closing of this valve lowers and raises, respectively, the concentration of said sorted clusters in each microreservoir as a function of the number of capsules undergoing formation in said encapsulation unit, each microreservoir also having a plurality of fine transverse outlet microchannels which are configured to allow expulsion of the phase containing said clusters with the exception of the latter, when said valve is closed.

11. A microfluidic system according to claim 1, wherein each of said encapsulation subunits communicates with one of said sorting microchannels by a coupling module configured to maintain laminar fluidic conditions between this sorting microchannel and the corresponding encapsulation subunit so as to form, for each size category of sorted clusters circulating in each sorting microchannel, a capsule of predetermined size which surrounds each cluster of this category as closely as possible.

* * * * *